United States Patent
Mizukami et al.

[11] Patent Number: 6,004,816
[45] Date of Patent: Dec. 21, 1999

[54] REAGENT AND METHOD FOR CLASSIFICATION AND COUNTING OF LEUKOCYTES

[75] Inventors: Toshihiro Mizukami, Hyogo-ken; Munetaka Ishiyama, Kumamoto; Takashi Sakata, Kakogawa, all of Japan

[73] Assignee: Sysmex Corporation, Kobe, Japan

[21] Appl. No.: 09/080,016

[22] Filed: May 15, 1998

[30] Foreign Application Priority Data

May 19, 1997 [JP] Japan .................... 9-128472

[51] Int. Cl.⁶ .................................................. G01N 31/00
[52] U.S. Cl. ..................... 436/10; 436/8; 436/17; 436/63; 436/164; 436/172; 436/800; 252/408.1
[58] Field of Search ....................... 436/8, 10, 17, 436/18, 63, 164, 172, 175, 800; 435/2; 252/408.1

[56] References Cited

U.S. PATENT DOCUMENTS

| | | | |
|---|---|---|---|
| 4,386,146 | 5/1983 | Kishino et al. | 430/95 |
| 4,933,293 | 6/1990 | Kuroda et al. | 436/63 |
| 4,957,870 | 9/1990 | Lee et al. | 436/63 |
| 5,175,109 | 12/1992 | Sakata et al. | 436/17 |
| 5,264,369 | 11/1993 | Sakata et al. | 436/63 |
| 5,296,378 | 3/1994 | Sakata et al. | 436/63 |
| 5,308,772 | 5/1994 | Sakata et al. | 436/63 |
| 5,413,938 | 5/1995 | Tsujino et al. | 436/63 |
| 5,436,134 | 7/1995 | Haugland et al. | 435/34 |
| 5,496,734 | 3/1996 | Sakata | 436/63 |
| 5,534,416 | 7/1996 | Millard et al. | 436/63 X |
| 5,821,127 | 10/1998 | Akai et al. | 436/10 |

*Primary Examiner*—Maureen M. Wallenhorst
*Attorney, Agent, or Firm*—Pearne, Gordon, McCoy & Granger LLP

[57] ABSTRACT

A reagent for classification and counting of leukocytes, the reagent containing at least one dye which has the following structural formula

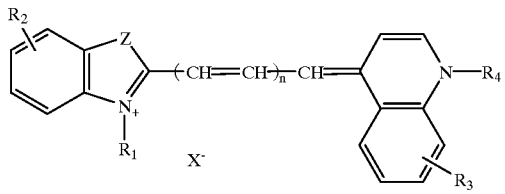

where $R_1$ is a hydrogen atom or an alkyl group, $R_2$ and $R_3$ each represent a hydrogen atom, a lower alkyl group or a lower alkoxy group, $R_4$ represents a hydrogen atom, an acyl group or an alkyl group, Z represents a sulfur atom, an oxygen atom, or a carbon atom having a lower alkyl group, n denotes 0, 1 or 2, and $X^-$ represents an anion, and specifically binds to RNA to increase in fluorescence intensity, and a method for classification and counting of leukocytes which uses the reagent, whereby abnormal cells such as immature leukocytes and abnormal leukocytes can be classified and counted easily and highly accurately, and at the same time, classification and counting of normal leukocytes as well as the counting of leukocytes can be performed.

9 Claims, 11 Drawing Sheets

REAGENT AND METHOD FOR CLASSIFICATION AND COUNTING OF LEUKOCYTES

BACKGROUND OF THE INVENTION

This invention relates to a reagent and a method for classification and counting of leukocytes by flow cytometry.

In the field of laboratory examination, the classification and counting of leukocytes can give very useful information for diagnosis of disease. For example, leukocytes in the normal peripheral blood usually include five normal types of leukocytes, i.e., lymphocytes, monocytes, neutrophils, eosinophils, and basophils, in constant proportions. In the presence of disease, the proportions of these leukocytes may vary. Measuring the proportions of the different types of leukocytes by classifying and counting these normal leukocytes is useful for obtaining information on the presence of disease.

Depending on the type of disease, immature leukocytes or erythrocytes which usually exist in the bone marrow and not in the peripheral blood, for example, immature granulocytes such as myeloblasts, promyelocytes, myelocytes or metamyelocytes, and erythroblasts, may appear in the peripheral blood in addition to these normal leukocytes. Abnormal leukocytes, such as lymphoblasts, atypical lymphocytes or abnormal lymphocytes, may also emerge. Detection of these cells, and their classification and counting, are of utmost importance for diagnosis of disease.

For leukocyte classification, it has been customary practice to prepare a blood smear, stain it appropriately, and observe the stained sample microscopically for classification and counting. In recent years, various full-automated differential leukocyte counters based on the principle of a flow cytometer have been provided. These devices permit highly precise classification of normal leukocytes, but did not make it possible to classify and count the above-mentioned abnormal cells, such as immature leukocytes, simultaneously with the classification and counting of normal leukocytes.

For instance, a reagent and a method which detect the appearance of immature leukocytes highly precisely by the principle of RF/DC measurement have been provided (Japanese Unexamined Patent Publication No. 6-273413). The method of this publication measures immature leukocytes electrically by utilizing their nature that under particular conditions, they are less destructible than normal leukocytes. It has also been suggested that their measurement can be made based on information on scattered light from them. However, this method aims only at the detection of immature leukocytes, and has excellent performance in their detection, but cannot classify and count normal leukocytes simultaneously with the measurement of immature leukocytes. Alternative methods should be performed for the classification and counting of normal leukocytes.

A different method that has been provided uses the principle of fluorometry to classify and count various immature leukocytes simultaneously with classifying leukocytes into four different populations (Japanese Unexamined Patent Publication No. 6-207942). With this method, normal leukocytes can be classified into only four populations at the same time, and basophils need to be measured separately in a different manner. A plurality of fluorescence signals also need to be measured, requiring a complicated, expensive apparatus.

A method for classifying and counting various immature leukocytes at the same time as the classification of leukocytes into five populations has also been provided (Japanese Unexamined Patent Publication No. 5-34251). This method requires a complicated detector for the classification of leukocytes into five populations. Two types of fluorescence information are also needed, thus involving a large, expensive apparatus.

SUMMARY OF THE INVENTION

An object of the present invention is to provide a reagent and a method capable of classifying and counting abnormal cells, such as immature leukocytes and abnormal leukocytes, easily and highly precisely, and simultaneously performing classification and counting of normal leukocytes, as well as counting of leukocytes.

The inventor of the present application has found that leukocytes can be classified into at least 5 populations easily by the use of a certain dye. That is, the present invention contains at least one dye which has the following structural formula

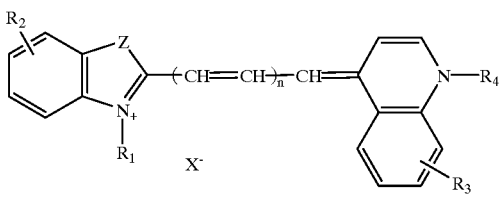

where $R_1$ is a hydrogen atom or an alkyl group, $R_2$ and $R_3$ each represent a hydrogen atom, a lower alkyl group or a lower alkoxy group, $R_4$ represents a hydrogen atom, an acyl group or an alkyl group, Z represents a sulfur atom, an oxygen atom, or a carbon atom having a lower alkyl group, n denotes 0, 1 or 2, and $X^-$ represents an anion, and specifically binds to RNA to increase in fluorescence intensity.

A method for leukocyte classification according to the present invention comprises the steps of:

1) mixing a blood sample with a hemolytic agent which lyses erythrocytes in the blood sample to such a degree as not to impede measurement, thereby bringing normal or abnormal cells to a state suitable for staining;

2) mixing a sample prepared in the step 1) with a dye which has the following structural formula

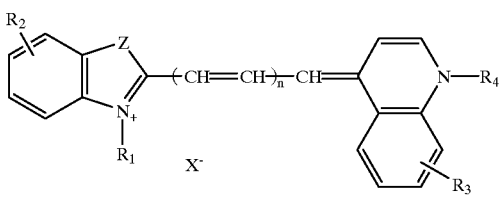

where $R_1$ is a hydrogen atom or an alkyl group, $R_2$ and $R_3$ each represent a hydrogen atom, a lower alkyl group or a lower alkoxy group, $R_4$ represents a hydrogen atom, an acyl group or an alkyl group, Z represents a sulfur atom, an oxygen atom or a carbon atom having a lower alkyl group, n denotes 0, 1 or 2, and $X^-$ represents an anion, and specifically binds to cellular RNA to increase in fluorescence intensity, thereby fluorescence-staining nucleated cells in the blood sample;

3) measuring an assay sample prepared in the step 2) with a flow cytometer to measure at least one scattered light and at least one fluorescence; and 4) classifying normal leukocytes into at least 5 populations, and counting them, by the use of differences in the scattered light and the fluorescence measured in the step 3).

The blood sample in the invention refers to a body fluid sample containing leukocytes, such as peripheral blood, bone marrow fluid, urine, or a blood sample collected by apheresis.

The abnormal cells in the invention refer to immature cells which usually exist in the bone marrow and not in the peripheral blood, for example, immature leukocytes including immature granulocytes (IG) such as myeloblasts (Blast), promyelocytes, myelocytes or metamyelocytes, abnormal leukocytes such as atypical lymphocytes (A-Lymph), lymphoblasts (L-Blast) or abnormal neutrophils (Ab-Neut), erythroblasts (nucleated red blood cells; NRBC) or cells which are usually not present in the peripheral blood.

The step of mixing a blood sample with a hemolytic agent which lyses erythrocytes in the blood sample to such a degree as not to impede measurement, thereby bringing normal or abnormal cells to a state suitable for staining, one of the steps in the present invention, refers to the step of mixing a blood sample with a suitable hemolytic agent. The purpose of this step is merely to form pores in the cell membrane of a leukocyte cell to be measured, the pores being of a sufficient size for at least dye molecules to pass through. The hemolytic agent used for this purpose is an aqueous solution of pH 4.5 to 11.0, preferably 5.0 to 10.0, which contains at least one cationic surfactant, at least one nonionic surfactant, and a buffer for maintaining a constant pH.

As the cationic surfactant, a quaternary ammonium salt type surfactant or a pyridinium salt type surfactant is preferred. Examples of the quaternary ammonium salt type surfactant and the pyridinium salt type surfactant are surfactants with a total carbon number of 9 to 30 expressed by the formula:

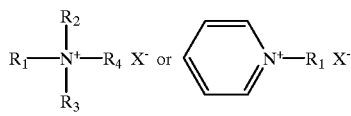

where $R_1$ represents an alkyl or alkenyl group having 6 to 18 carbon atoms, $R_2$ and $R_3$ each represent an alkyl or alkenyl group having 1 to 4 carbon atoms, $R_4$ represents an alkyl or alkenyl group having 1 to 4 carbon atoms, or a benzyl group, and X represents a halogen atom.

As the $R_1$ representing an alkyl or alkenyl group having 6 to 18 carbon atoms, hexyl, octyl, decyl, dodecyl or tetradecyl can be exemplified. A straight-chain alkyl group such as octyl, decyl or dodecyl, in particular, is preferred. Examples of the $R_2$ and $R_3$ representing an alkyl or alkenyl group having 1 to 4 carbon atoms are methyl, ethyl, propyl and butyl. Particularly preferred is an alkyl group with 1 to 3 carbon atoms such as methyl, ethyl or propyl. As the $R_4$ representing an alkyl or alkenyl group having 1 to 4 carbon atoms, methyl, ethyl, propyl or butyl can be quoted. Especially, an alkyl group with 1 to 3 carbon atoms such as methyl, ethyl or propyl is preferred.

As the nonionic surfactant, a polyoxyethylene series nonionic surfactant having the following formula is preferred:

$$R_1-R_2-(CH_2CH_2O)_n-H$$

where $R_1$ represents an alkyl, alkenyl or alkinyl group with 8 to 25 carbon atoms, $R_2$ represents —O—,

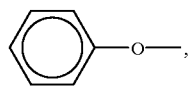

or —COO, and n denotes an integer of 10 to 50.

There is no restriction on the composition of the hemolytic agent, but the hemolytic agents described in Japanese Unexamined Patent Publication Nos. 6-207942 and 7-181177, for example, can be used preferably.

Furthermore, the incorporation into the hemolytic agent of at least one organic acid having at least one aromatic ring in a molecule or a salt thereof is preferred for the purpose of adjusting the scattered light intensity distribution of leukocytes so as to be more suitable for classification. For example, benzoic acid, phthalic acid, hippuric acid, salicylic acid, p-aminobenzenesulfonic acid or benzenesulfonic acid, or a salt of any of these acids can be used preferably as the organic acid or its salt. The incorporation of the organic acid increases the scattered light intensity of eosinophils, and eventually improves the separation of eosinophils from neutrophils. For instance, substantially only lateral scattered light is used to enable classification of leukocytes into 4 populations.

The pH of the hemolytic agent is 4.5 to 11.0, preferably 5.0 to 10.0. To maintain a constant pH, a buffer such as citrate, HEPES or phosphate is contained in the hemolytic agent. When the above-mentioned acid acts as a buffer, the buffer stated is not an absolutely necessary component. If the pH is too low, eosinophils and basophils are separated poorly, and it becomes difficult to classify normal leukocytes into 5 populations. However, it is possible to classify normal leukocytes into 3 categories (lymphocytes, monocytes, granulocytes) and to classify and count immature leukocytes and abnormal leukocytes.

Too high a pH is not preferred, because it will make leukocytes prone to damage.

As the dye which specifically binds to cellular RNA to increase in fluorescence intensity, there can be used a dye which has low fluorescence intensity in an RNA-free environment and increases in fluorescence intensity by binding to RNA.

A majority of abnormal cells such as immature leukocytes or abnormal leukocytes are rich in RNA as compared with normal leukocytes. Immature leukocytes, for example, are cells on the way to maturation, and thus perform various producing activities associated with cell maturation (e.g., protein synthesis), so that they may have an abundance of RNA.

For use In the reagent and method for leukocyte classification and counting of the present invention, any of the following dyes are preferred:

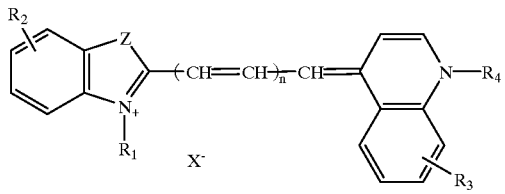

where $R_1$ is a hydrogen atom or an alkyl group, $R_2$ and $R_3$ each represent a hydrogen atom, a lower alkyl group or a lower alkoxy group, $R_4$ represents a hydrogen atom, an acyl group or an alkyl group, Z represents a sulfur atom, an oxygen atom, or a carbon atom having a lower alkyl group, n denotes 0, 1 or 2, and X⁻ represents an anion.

The above dyes have the property of markedly increasing in fluorescence intensity by binding to RNA.

Unexpectedly, the use of these dyes enables basophils to be classified simultaneously.

As stated above, these dyes increase in fluorescence intensity (have specificity) when bound to RNA, but often increase in fluorescence intensity even when bound to DNA. The dyes specific for DNA as well can be used in the present invention. However, fluorescence signals from DNA are superimposed on fluorescence signals from RNA, causing a tendency toward shrinking differences in fluorescence intensity between normal leukocytes and immature leukocytes or abnormal leukocytes. For the object of the present invention, therefore, the dyes with a low affinity (specificity) for DNA are more preferable.

To lessen the influence of their binding to DNA and enhance their specificity for RNA, we have synthesized those dyes of the aforementioned dyes in which at least one of $R_1$ and $R_4$ is a long-chain (carbon number: 6 to 18) alkyl group. We have used these dyes to classify and count normal and abnormal leukocytes.

As a result, it has been found that although the mechanism of action is not clear, the above dyes cannot pass through the cell nuclear membrane because of the presence of the long chain alkyl group in their molecular structure, or their binding to DNA molecules is inhibited owing to their steric hindrance. Hence, these dyes have been found to involve a smaller fluorescence increase due to DNA, and produce the advantage that fluorescence mainly ascribed to RNA can be measured. Thus, the separation of abnormal cells, such as immature leukocytes or abnormal leukocytes, from normal leukocytes can be improved markedly.

The larger the chain length (carbon number) of the long chain alkyl group, the more the increase in fluorescence intensity due to DNA is suppressed, and the higher the specificity for RNA becomes. The longer chain, on the other hand, tends to make the molecule more hydrophobic. Thus, the dyes become slightly soluble in water, and are difficult to handle, although not unusable. In view of these facts, the dyes in which $R_1$ or $R_4$ is an alkyl group with 6, 8 or 10 carbon atoms are particularly preferred.

The lower alkyl group or lower alkoxy group for $R_2$ and $R_3$ refers to a straight chain alkyl or alkoxy group having 1 to 8 carbon atoms. Preferred examples are methyl, methoxy, ethyl and ethoxy.

Preferred anions as X⁻ include, for example, halogen ions such as F⁻, Cl⁻, Br⁻ and I⁻, $CF_3SO_3^-$ and $BF_4^-$.

Preferred examples of the Z are a sulfur atom, an oxygen atom, or a carbon atom substituted by a lower alkyl group such as methyl, ethyl or isopropyl.

The concentration of the dye differs according to the type of the dye used. Generally, its concentration is 0.001 to 1,000 ppm, preferably 0.01 to 100 ppm, more preferably 0.1 to 10 ppm. This concentration is the concentration in the reagent for leukocyte classification and counting, and when a staining solution and the hemolytic agent are separately prepared, the concentration refers to the concentration in a mixture of the staining solution and the hemolytic agent.

The reagent for leukocyte classification and counting of the present invention can be prepared by dissolving the above dye in a water-soluble organic solvent such as ethylene glycol, methanol or DMSO, storing the solution as a staining solution, and adding the staining solution, when in use, to a sample prepared by mixing a blood sample with the hemolytic agent. Alternatively, the dye can be incorporated into the hemolytic agent to make a one-component type reagent.

The so prepared assay sample is measured with a flow cytometer to determine at least one scattered light and at least one fluorescence.

The scattered light in the present invention refers to scattered light that can be measured with a commercially available flow cytometer. This scattered light includes, for example, lateral scattered light, forward low-angle scattered light (light-receiving angle: nearly 0 to 5 degrees), and forward high-angle scattered light (light-receiving angle: nearly 5 to 20 degrees). Scattered light having such a scattering angle as to reflect information on the sizes or internal structure of leukocytes is selected as the scattered light of the invention. The most preferable one is lateral scattered light.

The use of one or more types of scattered light can increase the precision of classification.

The use of forward low-angle scattered light, in particular, gives information on the sizes of cells. For example, its use enables the present invention to detect abnormal cells changed only in size and involving no increase in RNA content, as in hairy cell leukemia.

The use of forward high-angle scattered light, on the other hand, gives information which is intermediate between the information obtained with the use of forward low-angle scattered light and the information obtained with the use of lateral scattered light. In short, information including the cellular size information and the cellular internal structure information is obtained.

Fluorescence is emitted from the dye bound to cell components such as RNA and DNA. Depending on the type of the dye used, the preferred wavelength of light to be received is selected.

The light source for the flow cytometer is not restricted, but may be a light source with a wavelength suitable for the excitation of the dye. For example, an argon laser, an He—Ne laser, a red semiconductor laser, or a mercury arc lamp is used. Especially, the semiconductor laser is preferred, because it is very inexpensive and small in size compared with the gas laser. Thus, it can markedly lower the equipment cost, and can further reduce the size of the equipment.

The step of "classifying normal leukocytes into at least 5 populations, and counting them, by the use of differences in the scattered light and the fluorescence measured" has the following contents: (1) When a scattergram (a two-dimensional distribution diagram) is drawn with lateral scattered light on the X axis and red fluorescence on the Y axis, for example, white blood cells are grouped into respective cell populations. (2) These cell populations are analyzed with suitable analytical software to calculate the numbers of the leukocytes in each cell population and the proportions of the respective cell populations. For example, a window surrounding each cell population is provided, and the number of the cells in each window is counted, whereby the number of the cells in each leukocyte population and the proportions of the respective leukocyte populations can be calculated.

When the reagent and method of the present invention are used, not only can normal leukocytes be classified into at least 5 populations and counted by the type of population, but can the classification and counting of abnormal cells be performed simultaneously with their classification and counting. The abnormal cells suitable for classification and counting by the use of the reagent and method of the present invention are cells with RNA content increased over normal cells. For example, they are one or more members selected from the group consisting of immature granulocytes, myeloblasts, erythroblasts and atypical lymphocytes.

The present invention also provides a reagent kit for classification and counting of leukocytes, including a reagent comprising:

1) a hemolytic agent which lyses erythrocytes in a blood sample to such a degree as not to impede measurement, thereby bringing normal or abnormal cells to a state suitable for staining; and
2) a staining solution containing at least one dye which has the following structural formula

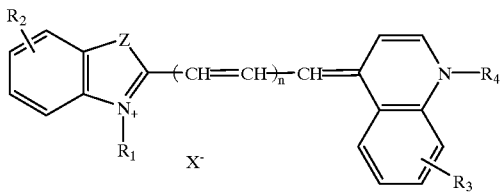

where $R_1$ is a hydrogen atom or an alkyl group, $R_2$ and $R_3$ each represent a hydrogen atom, a lower alkyl group or a lower alkoxy group, $R_4$ represents a hydrogen atom, an acyl group or an alkyl group, Z represents a sulfur atom, an oxygen atom or a carbon atom having a lower alkyl group, n denotes 0, 1 or 2, and $X^-$ represents an anion, and specifically binds to RNA to increase in fluorescence intensity.

DETAILED DESCRIPTION OF THE PREFERRED EMBODIMENTS

Figure 1:
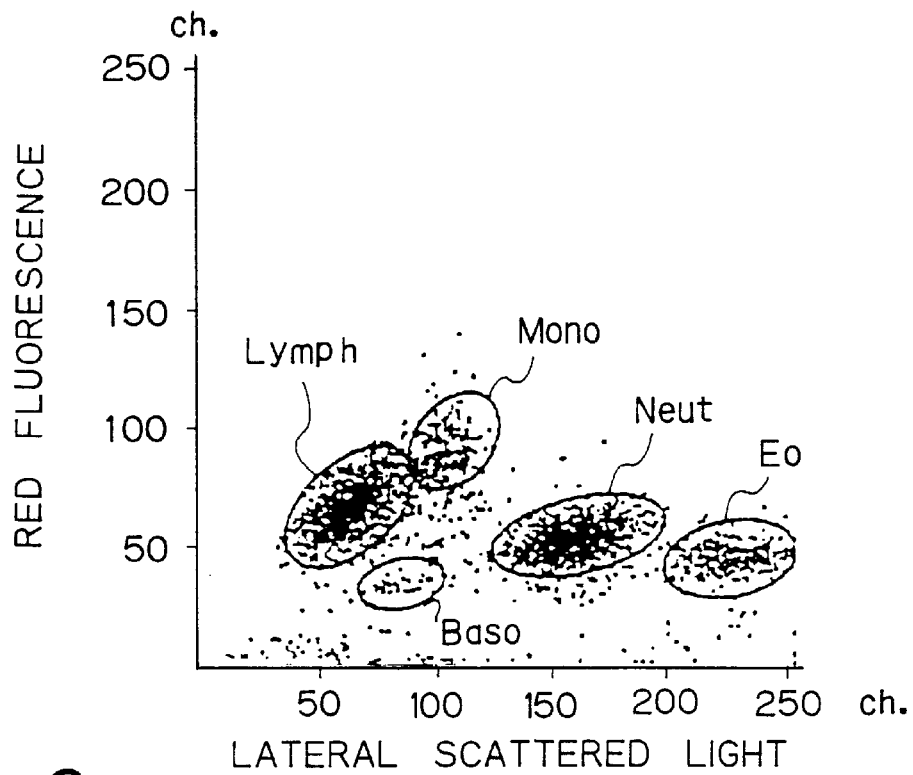
FIG. 1 is a lateral scattered light-red fluorescence scattergram of a normal subject's blood sample measured using the reagent of Example 3.

The present invention will now be described in detail by way of the following Examples, but various changes and modifications may be made in the present invention. Thus, the scope of the present invention is not restricted by these examples.

In the accompanying drawings, the abbreviations have the following meanings:

| Lymph: | Lymphocytes | Eo: | Eosinophils |
| Mono: | Monocytes | Baso: | Basophils |
| Neut: | Neutrophils | WBC: | While blood cells |

-continued

| | | | |
|---|---|---|---|
| IG: | Immature granulocytes | Blast: | or leukocytes Myeloblasts |
| NRBC: | Nucleated red blood cells or erythroblasts | | |
| A-Lymph: | Atypical leukocytes | | |

Example 1 Synthesis of Dye Compound A

Dye Compound A ($R_1$=methyl, $R_2$, $R_3$=H, $R_4$=n-octyl, n=1, Z=S, X=$CF_3SO_3^-$) was produced in the following manner:

One equivalent of 3-methyl-2-methylbenzothiazolium methanesulfate and three equivalents of N,N-diphenylformamidine were heated in acetic acid, with stirring, for 1.5 hours on an oil bath of 90° C. The reaction mixture was poured into hexane, and a red oily matter was further suspended in and washed with hexane to remove acetic acid. The crude product was recrystallized from ethyl acetate-hexane (yield: 48%). To the crystals, one equivalent of 1-octyl lepidinium trifluorate and pyridine were added, and the mixture was heated, with stirring, for 3 hours on an oil bath of 90° C. The reaction mixture was concentrated, and the residual blue crude product was purified with methanol-chloroform by flush chromatography (yield: 62%).

In this manner, Dye Compound A ($R_1$=methyl, $R_2$, $R_3$=H, $R_4$=n-octyl, n=1, Z=S, X=$CF_3SO_3^-$) was obtained as a deep dark blue powder.

TLC (silica gel, 10% methanol-methylene chloride): Rf=0.5
$^1$H-NMR ($CDC_{l3}$) δ ppm (TMS): 0.88 (t,3H) 1.28 (bR, 10H) 1.64 (s,2H) 1.82 (bR,2H) 3.60 (s,3H) 4.23 (t,2H) 6.35 (d,1H) 6.82–7.26 (m,2H) 7.39–7.90 (m,6H) 8.10–8.26 (dd, 2H) IR (cm$^{-1}$): 1625, 1560, 1540, 1520, 1480, 1460, 1410, 1400, 1310, 1260, 1210, 1150, 1130, 740, 640 MASS (FAB positive) m/z=429 TLC 95.7% (10% methanol-methylene chloride) Maximum absorption spectrum 629 nm (methanol)

Example 2 Synthesis of Dye Compound B

Dye Compound B ($R_1$=hexyl, $R_2$, $R_3$=H, $R_4$=methyl, n=1, Z=S, X=$CF_3SO_3^-$) was produced in the following manner:

One equivalent of 3-hexyl-2-methylbenzothiazolium trifluorate and four equivalents of N,N-diphenylformamidine were heated in acetic acid, with stirring, for 10 hours on an oil bath of 90° C. The reaction mixture was concentrated, and the residual crude product was purified with hexane-ethyl acetate by flush chromatography (yield: 27%). To the product, 1.3 equivalents of 1-methyl lepidinium iodide and pyridine were added, and the mixture was heated, with stirring, for 3 hours on an oil bath of 90° C. The reaction mixture was concentrated, and the residual blue crude product was purified with methanol-chloroform by flush chromatography (yield: 75%).

In this manner, Dye Compound B ($R_1$=hexyl, $R_2$, $R_3$=H, $R_4$=methyl, n=1, Z=S, X=$CF_3SO_3^-$) was obtained as a deep dark blue powder.

TLC (silica gel, 10% methanol-methylene chloride): Rf=0.5
$^1$-NMR ($CDCl_3$) δ ppm (TMS): 0.90 (t,3H) 1.17–1.81 (m,12H) 4.12 (s,3H) 6.50 (m,1H) 6.96–8.26 (m,10H) IR (cm$^{-1}$): 1620, 1560, 1530, 1510, 1480, 1460, 1410, 1380, 1310, 1250, 1210, 1150, 1100, 750, 640 MASS (FAB positive) m/z=401 TLC 93.0% (10% methanol-methylene chloride) Maximum absorption spectrum 629 nm (methanol)

Example 3 Formulation of Reagent for Classification and Counting of Leukocytes A reagent of the following composition was prepared:

| | | |
|---|---|---|
| HEPES | 10 mM | Commercially available product |
| Disodium phthalate | 20 mM | Commercially available product |
| BC30TX (polyoxyethylene (30) cetyl ether) | 1500 ppm | Nikko Chemicals |
| Lauryl trimethylammonium chloride | 550 ppm | Commercially available product |
| Dye Compound A | 0.5 ppm | |
| pH adjusted to 7.0 with NaOH | | |

To 1.0 ml of the above reagent, 30 μl of anticoagulant-treated blood from a normal subject was added, and the mixture was reacted for 40 seconds at 35° C. Then, the reaction mixture was measured for lateral scattered light, forward low-angle scattered light, and fluorescence with a flow cytometer (FCM).

The light source used was a red semiconductor laser operating at 633 nm. The fluorescence measured was a fluorescence with a wavelength of 660 nm or more (red fluorescence).

FIG. 1 is a scattergram with lateral scattered light taken on the X axis and red fluorescence taken on the Y axis.

Figure 2:
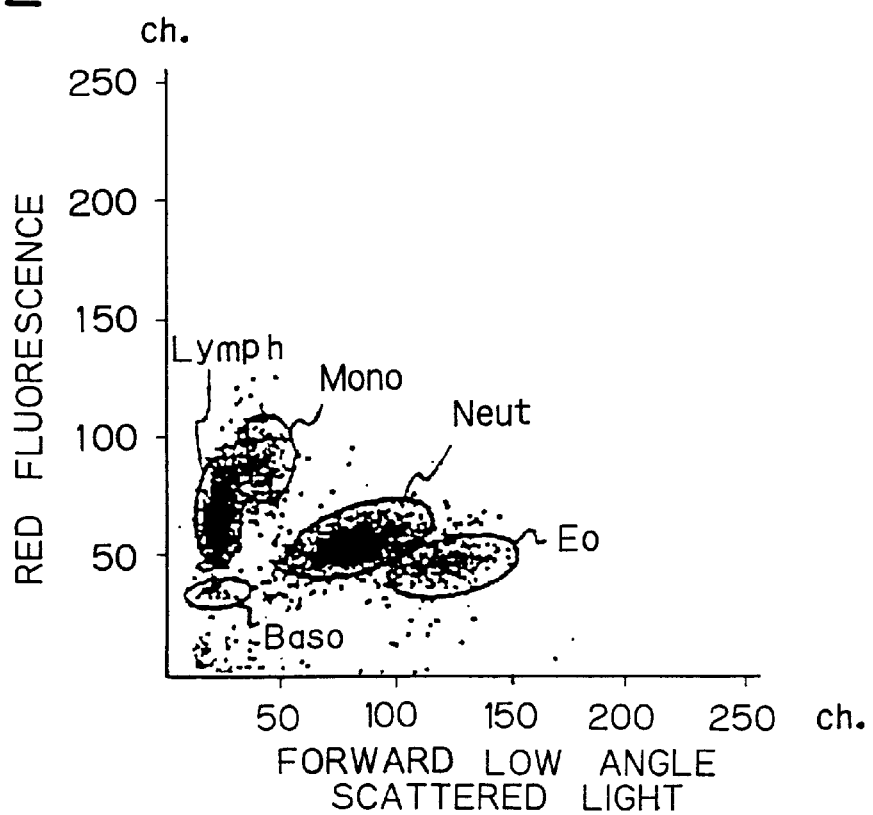
FIG. 2 is a forward low-angle scattered light-red fluorescence scattergram of the normal subject's blood sample measured using the reagent of Example 3.

FIG. 2 is a scattergram with forward low-angle scattered light taken on the X axis and red fluorescence taken on the Y axis.

Leukocytes were classified into 5 populations, i.e., lymphocytes, monocytes, neutrophils, eosinophils and basophils.

Figure 3:
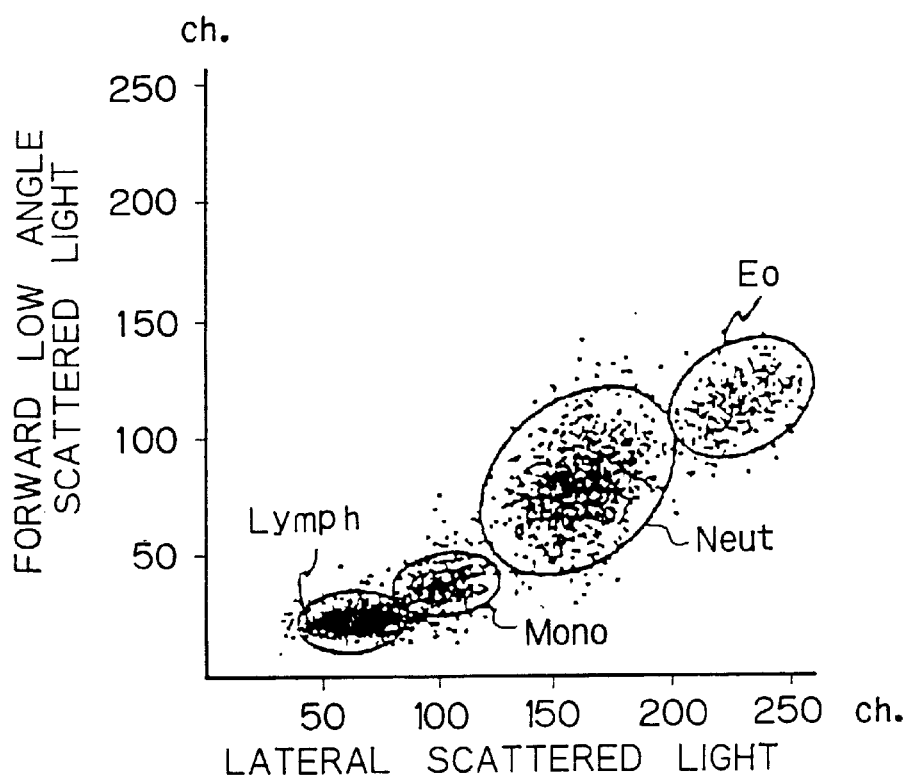
FIG. 3 is a lateral scattered light-forward low-angle scattered light scattergram of the normal subject's blood sample measured using the reagent of Example 3.
Figure 4:
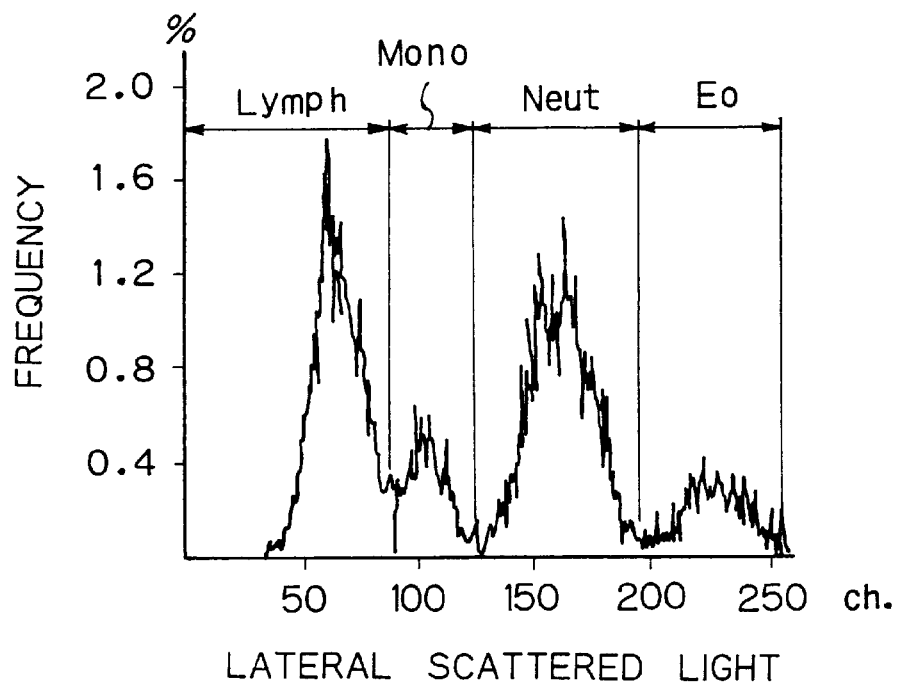
FIG. 4 is a lateral scattered light histogram of the normal subject's blood sample measured using the reagent of Example 3.
Figure 5:
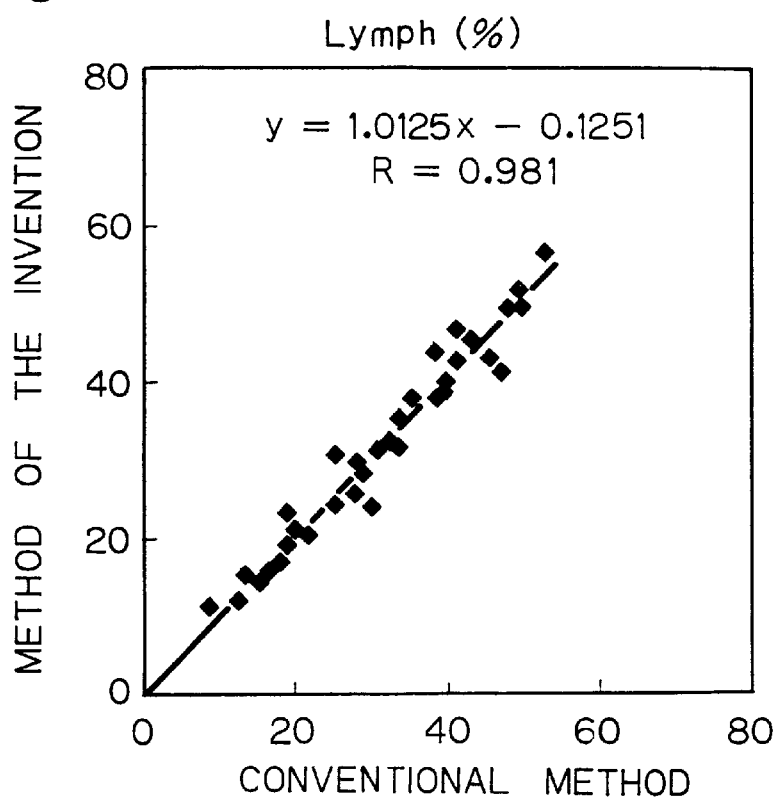
FIG. 5 is a graph showing the correlation between the percentage of lymphocytes measured by a conventional method (SE-9000, TOA MEDICAL ELECTRONICS CO., LTD.) and that measured by the method for classification and counting of Example 3.
Figure 6:
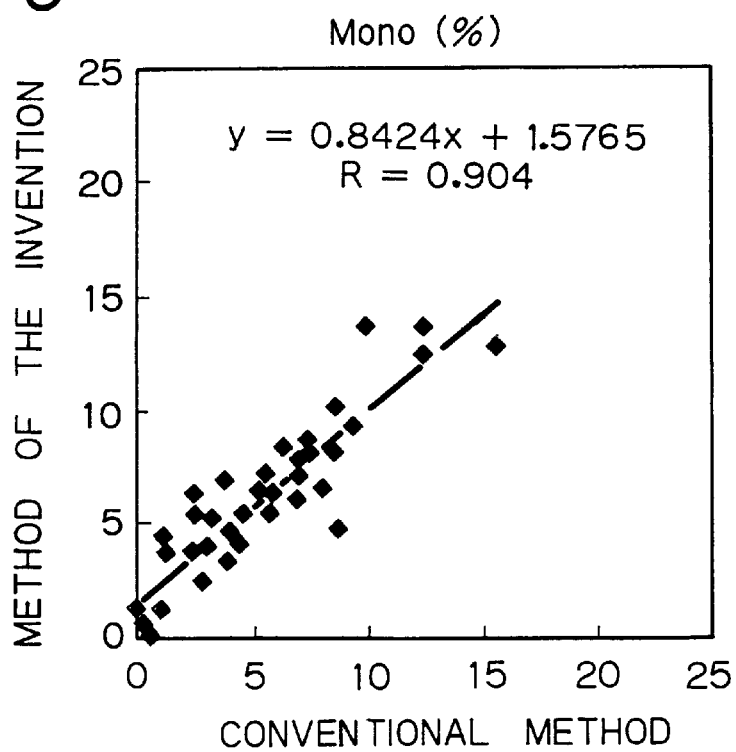
FIG. 6 is a graph showing the correlation between the percentage of monocytes measured by the conventional method (SE-9000, TOA MEDICAL ELECTRONICS CO., LTD.) and that measured by the method for classification and counting of Example 3.
Figure 7:
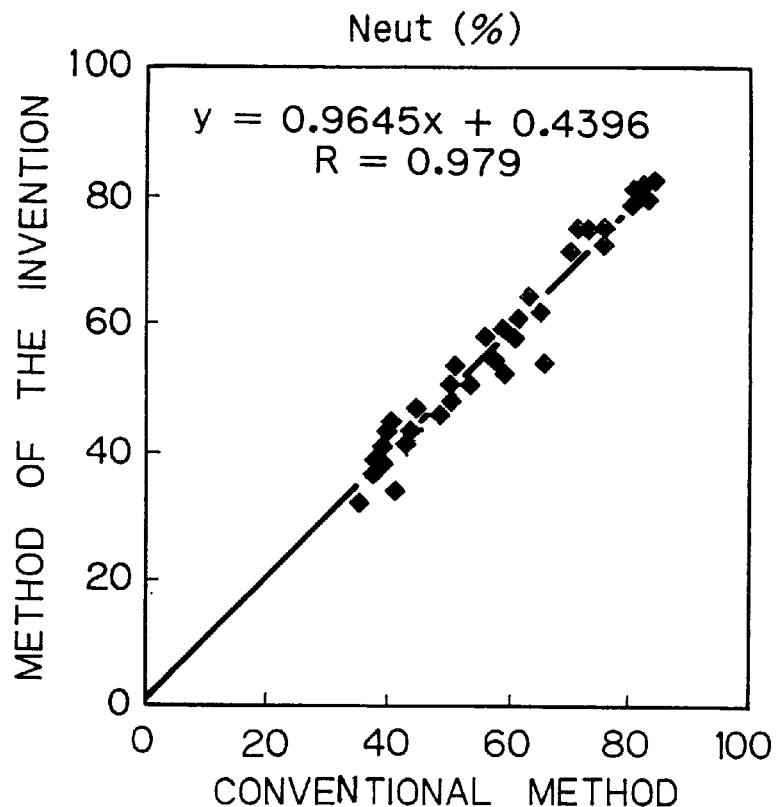
FIG. 7 is a graph showing the correlation between the percentage of neutrophils measured by the conventional method (SE-9000, TOA MEDICAL ELECTRONICS CO., LTD.) and that measured by the method for classification and counting of Example 3.
Figure 8:
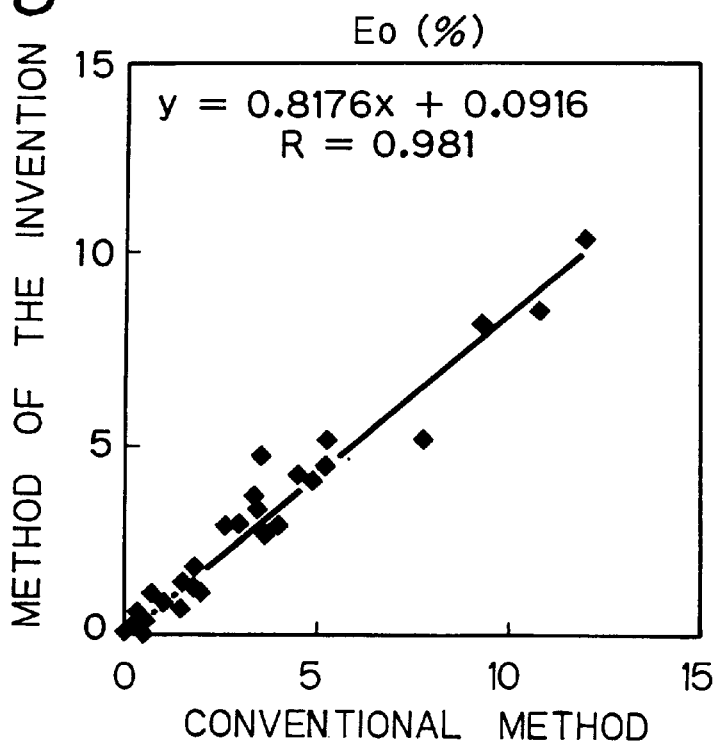
FIG. 8 is a graph showing the correlation between the percentage of eosinophils measured by the conventional method (SE-9000, TOA MEDICAL ELECTRONICS CO., LTD.) and that measured by the method for classification and counting of Example 3.
Figure 9:
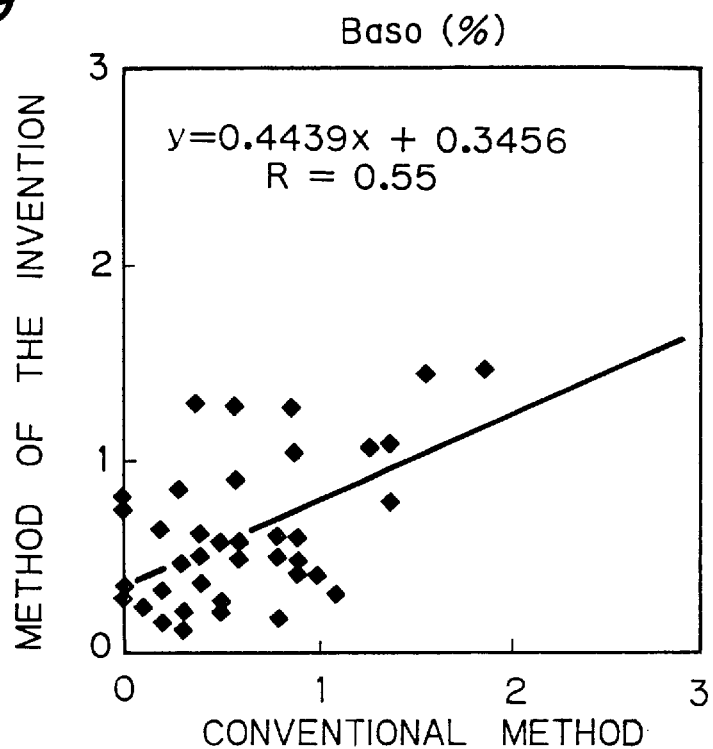
FIG. 9 is a graph showing the correlation between the percentage of basophils measured by the conventional method (SE-9000, TOA MEDICAL ELECTRONICS CO., LTD.) and that measured by the method for classification and counting of Example 3.

For information, FIG. 3 shows a scattergram with lateral scattered light taken on the X axis and forward low-angle scattered light taken on the Y axis, while FIG. 4 shows a histogram of the lateral scattered light intensities. Leukocytes were classified into 4 populations, i.e., lymphocytes, monocytes, neutrophils and eosinophils.

A window was provided for each population, and the number of the cells in each window and the proportions of the cells in the respective windows were calculated.

FIGS. 5 to 9 are each a graph showing the correlation between the percentage of leukocytes measured by a conventional method (SE-9000, TOA MEDICAL ELECTRONICS CO., LTD.) and that measured by the method of the present invention (FIG. 1).

Figure 10:
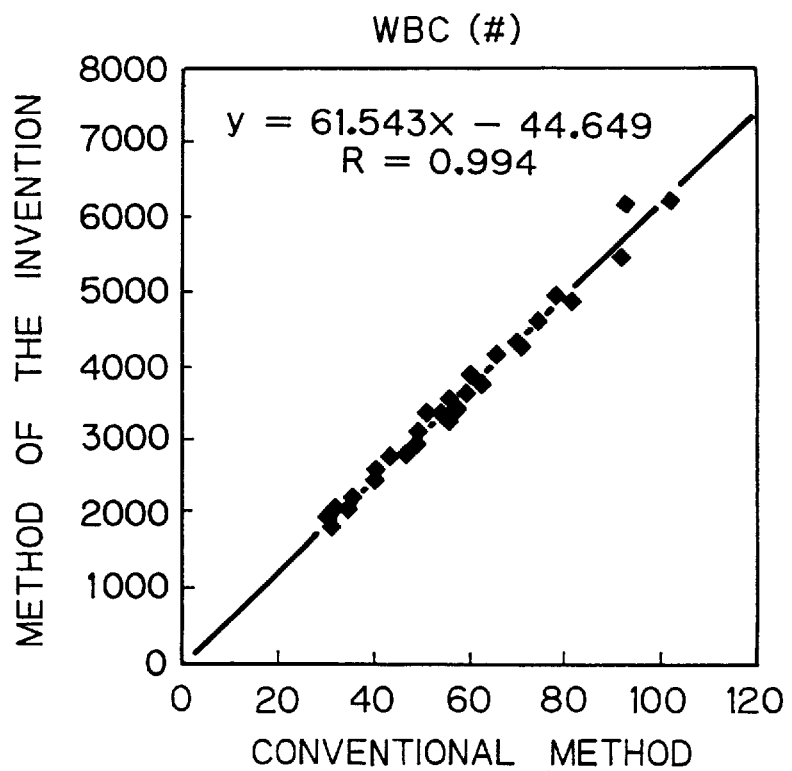
FIG. 10 is a graph showing the correlation between a WBC count determined by the conventional method (SE-9000, TOA MEDICAL ELECTRONICS CO., LTD.) and that determined by the method for classification and counting of Example 3.

FIG. 10 is a graph showing the correlation between a WBC count determined by the conventional method (SE-9000, TOA MEDICAL ELECTRONICS CO., LTD.) and that determined by the method of the present invention (FIG. 1).

A high correlation was noted between any parameters measured by the conventional method and those measured by the method of the present invention.

Measurements by the conventional method were performed using the following reagents in a full-automated manner by means of SE-9000:

WBC count: Measured after adding blood to a 1:1 mixture of Cellpack-3D(II)™ (TOA MEDICAL ELECTRONICS CO., LTD.) and Stromatolyzer EO(II)™ (TOA MEDICAL ELECTRONICS CO., LTD.).

Lymphocytes and monocytes: Measured after hemolysis with Cellpack-3D(II)™ (TOA MEDICAL ELECTRONICS CO., LTD.), and then adding Stromatolyzer 3D(II)™ (TOA MEDICAL ELECTRONICS CO., LTD.).

Eosinophils: Measured using Stromatolyzer EO(II)™ (TOA MEDICAL ELECTRONICS CO., LTD.).

Basophils: Measured using Stromatolyzer BA(II)™ (TOA MEDICAL ELECTRONICS CO., LTD.).

---

Neutrophils: Calculated from the equation (WBC count) − {(lymphocyte count) + (monocyte count) + (eosinophil count) + (basophil count)}

---

Figure 11:
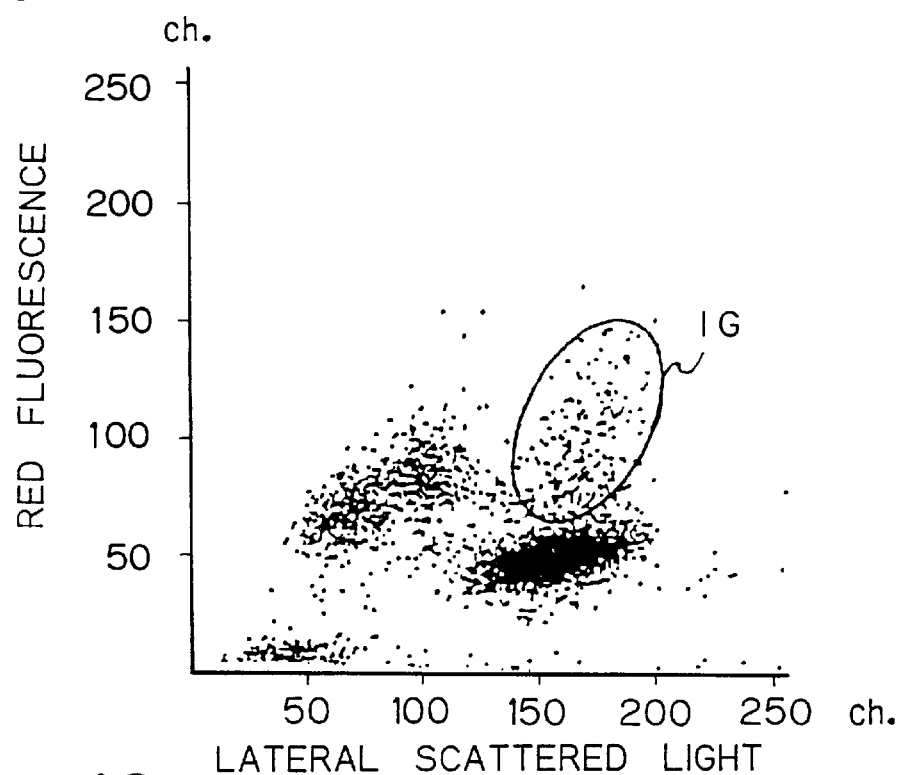
FIG. 11 is a lateral scattered light-red fluorescence scattergram of a sample measured using the reagent of Example 3, the sample showing the appearance of immature granulocytes (metamyelocytes, myelocytes)
Figure 12:
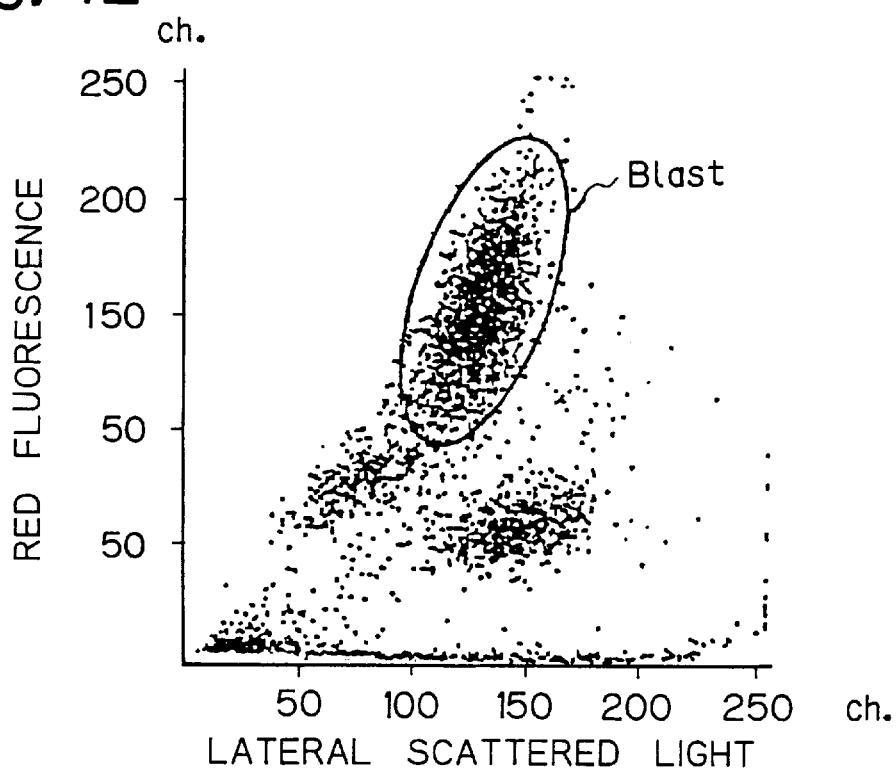
FIG. 12 is a lateral scattered light-red fluorescence scattergram of a sample measured using the reagent of Example 3, the sample showing the appearance of myeloblasts.
Figure 13:
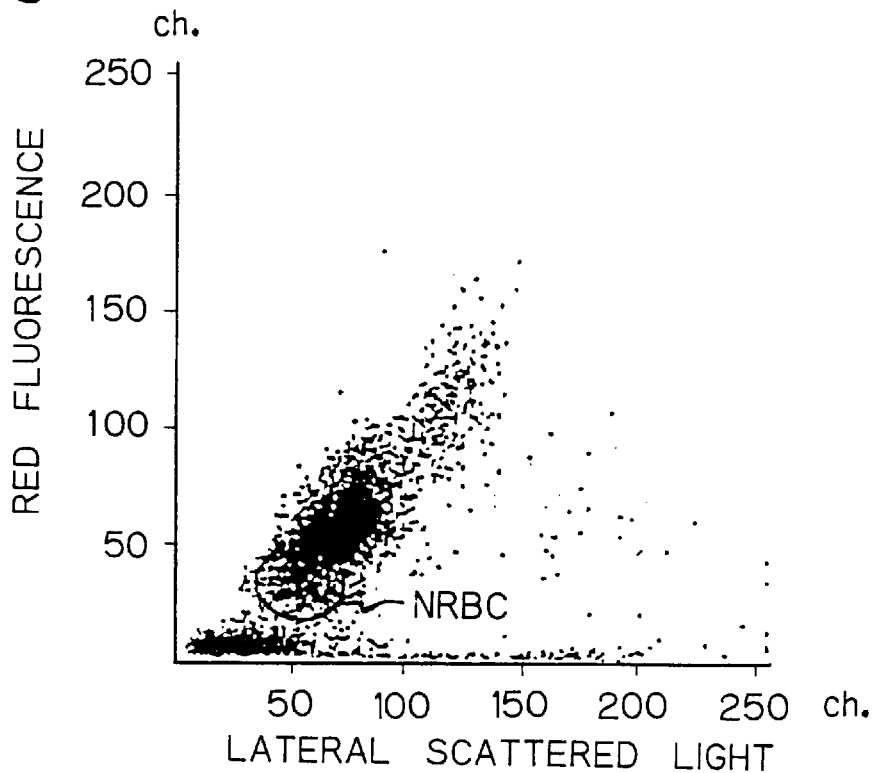
FIG. 13 is a lateral scattered light-red fluorescence scattergram of a sample measured using the reagent of Example 3, the sample showing the appearance of erythroblasts.
Figure 14:
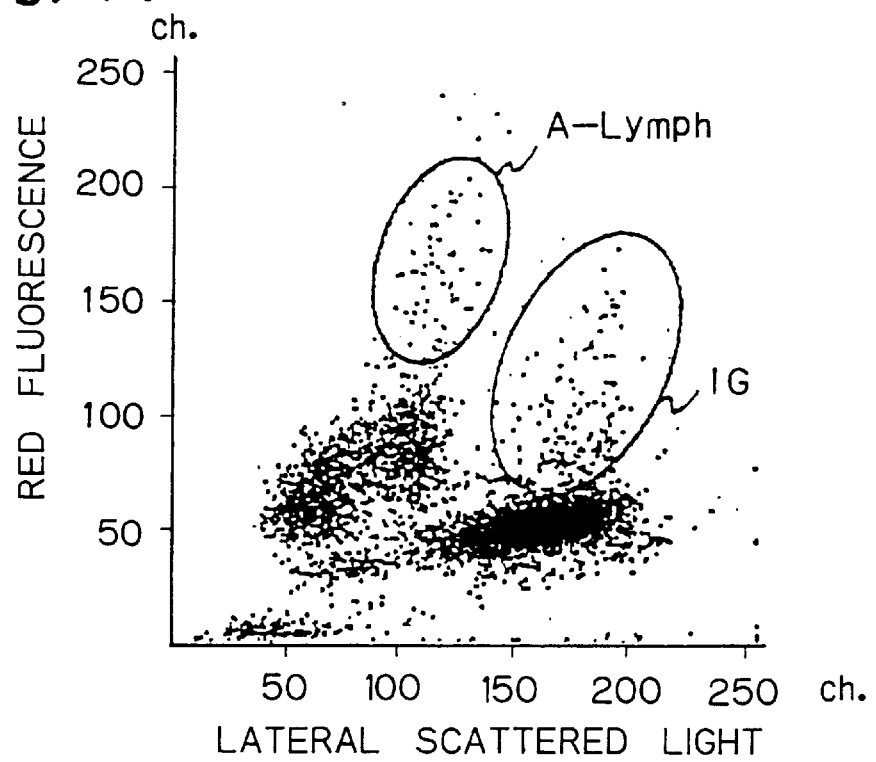
FIG. 14 is a lateral scattered light-red fluorescence scattergram of a sample measured using the reagent of Example 3, the sample showing the appearance of atypical lymphocytes and immature granulocytes.

Example 4 Classification and Counting of Samples in which Immature Granulocytes or Abnormal Leukocytes Appeared Using the reagent and method of Example 3, the following samples were measured:

Sample in which immature granulocytes (metamyelocytes, myelocytes) appeared (FIG. 11)
    4.5% for the conventional method (visual inspection), 4.0% for the method of the invention Sample in which myeloblasts appeared (FIG. 12)
    81.5% for the conventional method, 85.1% for the method of the invention Sample in which erythroblasts appeared (FIG. 13)
    25% for the conventional method, 21.5% for the method of the invention Sample in which atypical lymphocytes and immature granulocytes appeared (FIG. 14)

Atypical lymphocytes: 2.0% for the conventional method, 1.89% for the method of the invention Immature granulocytes: 2.0% for the conventional method, 2.17% for the method of the invention Any immature granulocytes and abnormal leukocytes were clearly distinguished from normal leukocytes, classified and counted. According to the conventional method, a smear was double stained by May-Grünwald-Giemsa staining, and leukocytes were classified and counted microscopically (magnification:×1,000) by 200's.

Example 5 Formulation of Reagent

| | |
|---|---|
| HEPES | 10 mM Commercially available product |
| Disodium phthalate | 20 mM Commercially available product |
| BC30TX (polyoxyethylene (30) cetyl ether) | 1500 ppm Nikko Chemicals |
| Lauryl trimethylammonium chloride | 550 ppm Commercially available product |
| Dye | Arbitrary amount |
| pH adjusted to 7.0 with NaOH | |

When the following dye was used:
DQTCI ($R_1$, $R_4$=ethyl, $R_2$, $R_3$=H, Z=S, $X^-$=$I^-$, n=1) 0.1 ppm Lambda Physik

| | |
|---|---|
| Dye Compound A | 0.5 ppm |
| Dye Compound B | 0.3 ppm |

To 1.0 ml of the above reagent, 30 μl of anticoagulant-treated blood was added, and the mixture was reacted for 40 seconds at 35° C. Then, the reaction mixture was measured for lateral scattered light and fluorescence with FCM. The assay samples were normal samples, and samples in which immature granulocytes appeared. The light source used was a red semiconductor laser operating at 633 nm. The fluorescence measured was a fluorescence with a wavelength of 660 nm or more. The light source and the wavelength of fluorescence were the same as in Example 3.

Figure 15:
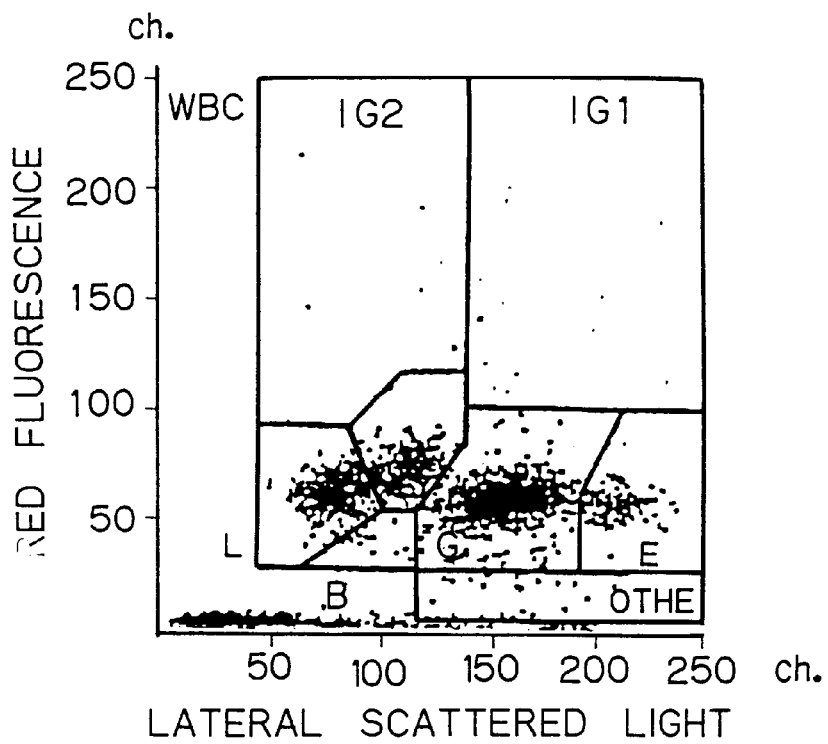
FIG. 15 is a lateral scattered light-fluorescence scattergram of a normal sample measured using Thiazole Blue as a dye in Example 5.
Figure 16:
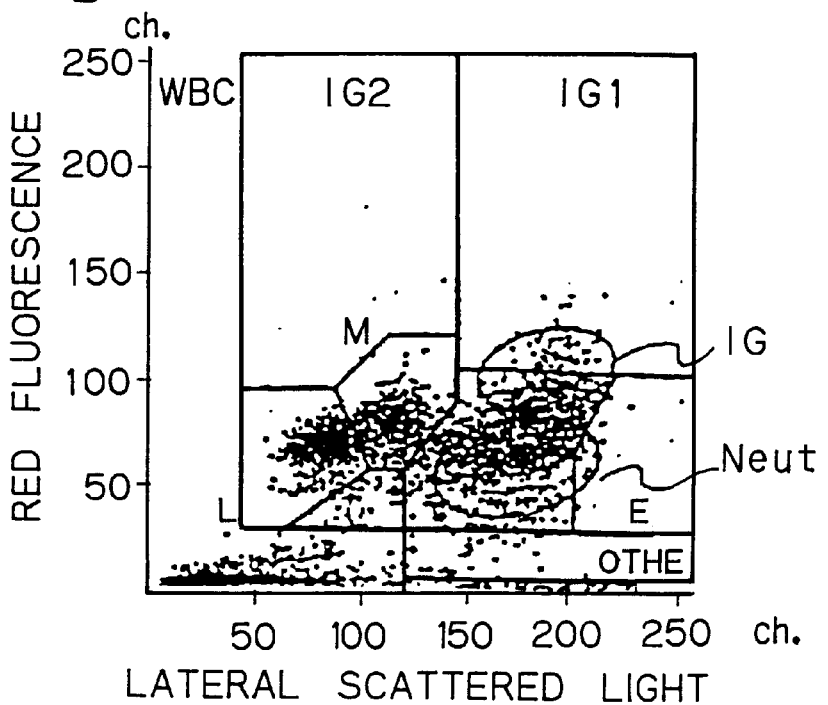
FIG. 16 is a lateral scattered light-fluorescence scattergram of a sample measured using Thiazole Blue as a dye in Example 5, the sample showing the appearance of immature granulocytes.
Figure 17:
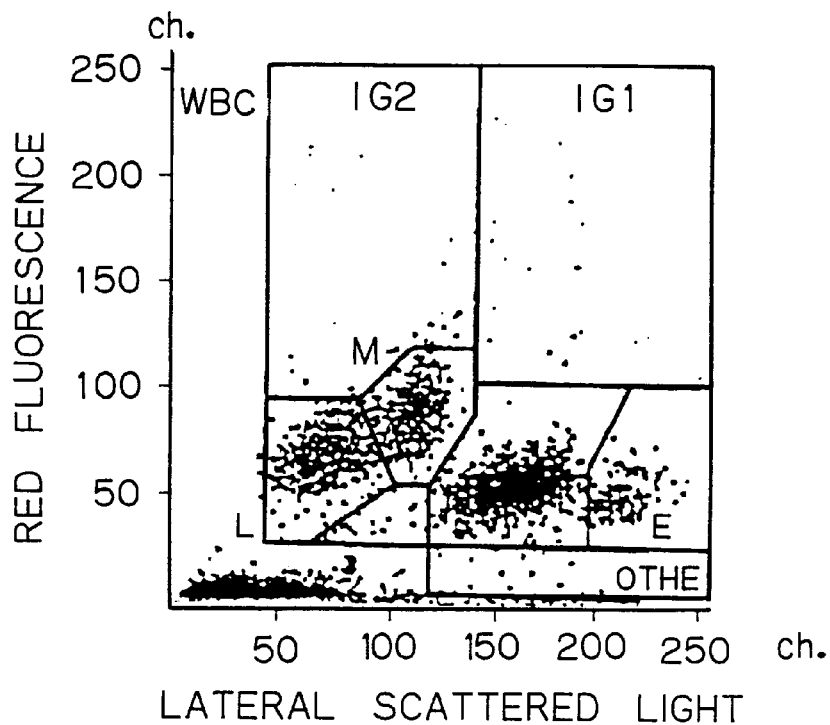
FIG. 17 is a lateral scattered light-fluorescence scattergram of a normal sample measured using Dye Compound A as a dye in Example 5.
Figure 18:
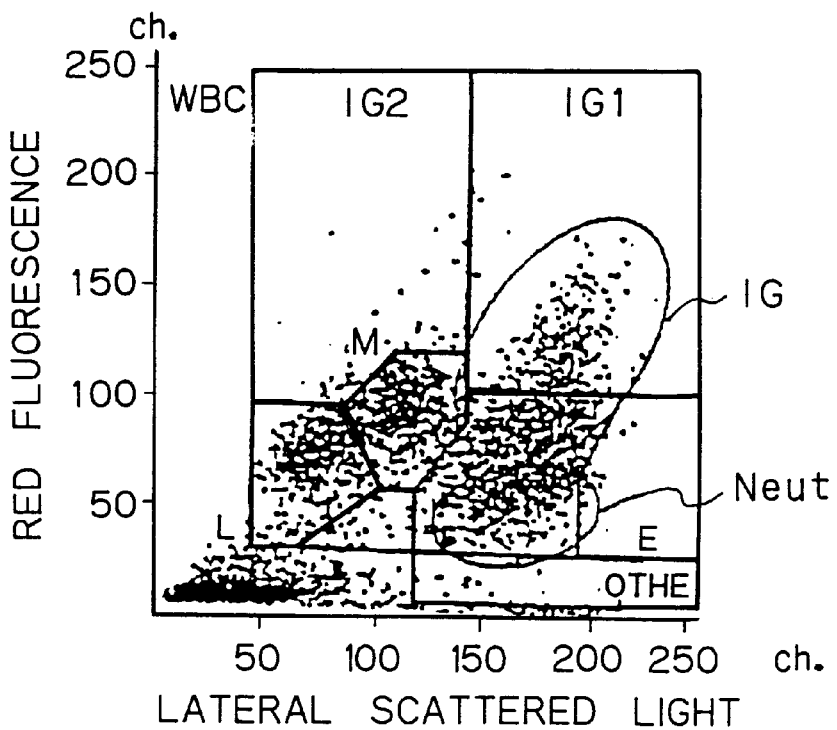
FIG. 18 is a lateral scattered light-fluorescence scattergram of a sample measured using Dye Compound A as a dye in Example 5, the sample showing the appearance of immature granulocytes.
Figure 19:
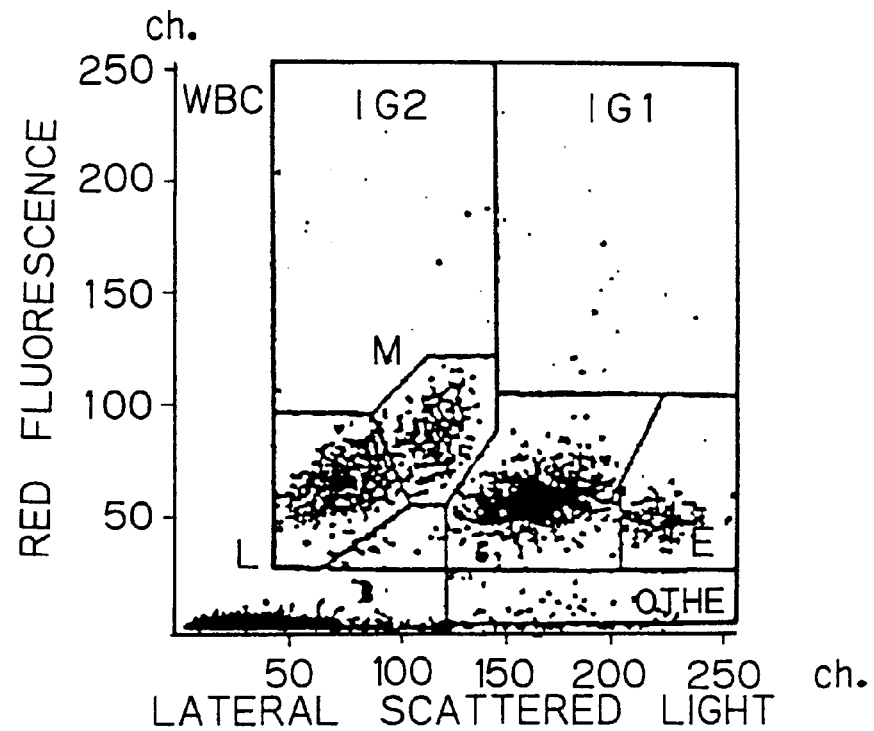
FIG. 19 is a lateral scattered light-fluorescence scattergram of a normal sample measured using Dye Compound B as a dye in Example 5.
Figure 20:
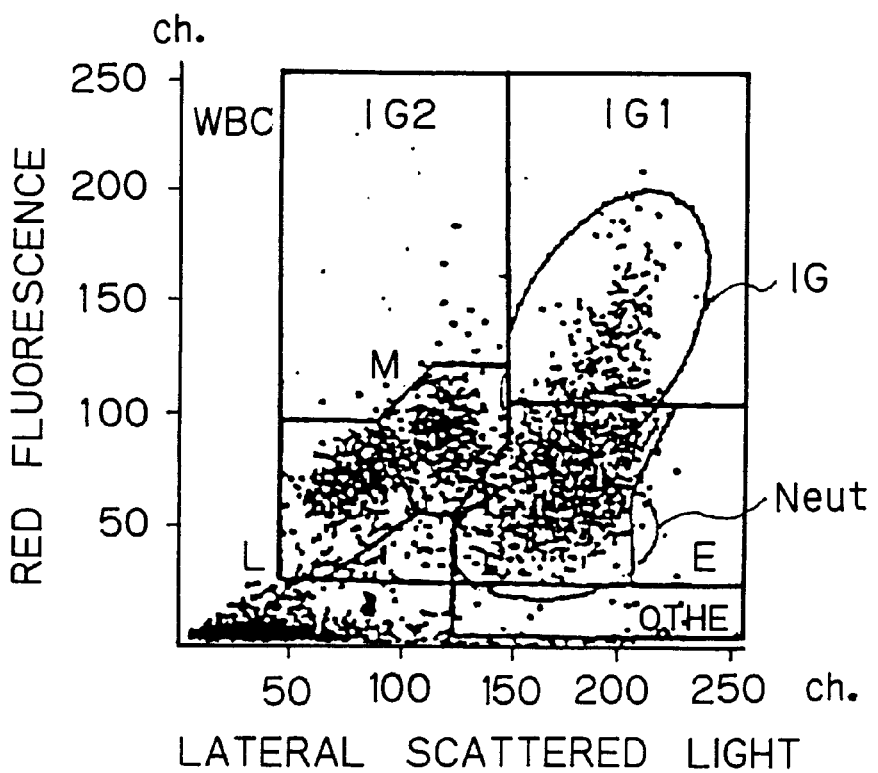
FIG. 20 is a lateral scattered light-fluorescence scattergram of a sample measured using Dye Compound B as a dye in Example 5, the sample showing the appearance of immature granulocytes.

FIGS. 15 to 16 are scattergrams obtained using Thiazole Blue. FIGS. 17 to 18 are scattergrams obtained using Dye Compound A. FIGS. 19 to 20 are scattergrams obtained using Dye Compound B.

When $R_1$ and $R_4$ were each a lower alkyl group, it was difficult to distinguish between normal neutrophils and immature granulocytes. When a long chain alkyl group was introduced, by contrast, it became possible to distinguish between normal neutrophils and immature granulocytes clearly.

Example 6 Formulation of Reagent

| | |
|---|---|
| HEPES | 10 mM Commercially available product |
| BC30TX (polyoxyethylene (30) cetyl ether) | 1500 ppm Nikko Chemicals |
| Lauryl trimethylammonium chloride | 550 ppm Commercially available product |
| Dye Compound A | 0.5 ppm |
| Acid | 20 mM Commercially available product |
| pH adjusted to 7.0 with NaOH | |

As the acid, citric acid or phthalic acid was used.

To 1.0 ml of the above reagent, 30 μl of anticoagulant-treated blood from a normal subject was added, and the mixture was reacted for 40 seconds at 35° C. Then, the reaction mixture was measured for lateral scattered light and fluorescence with FCM. The light source used was a red semiconductor laser operating at 633 nm. The fluorescence measured was a fluorescence with a wavelength of 660 nm or more (red fluorescence).

Figure 21:
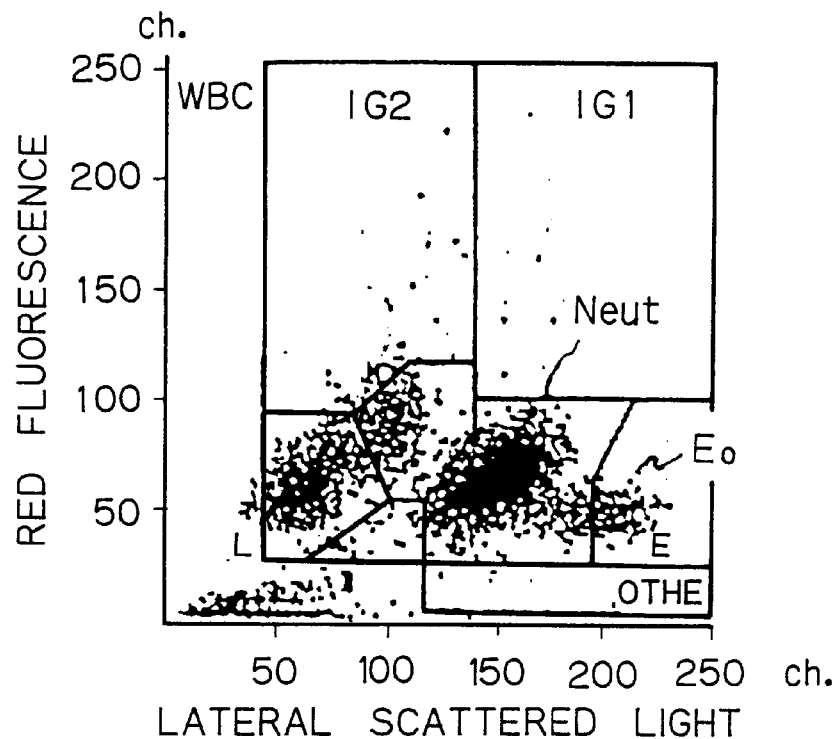
FIG. 21 is a lateral scattered light-fluorescence scattergram of a normal subject's blood sample measured using citric acid as an acid in Example 6.
Figure 22:
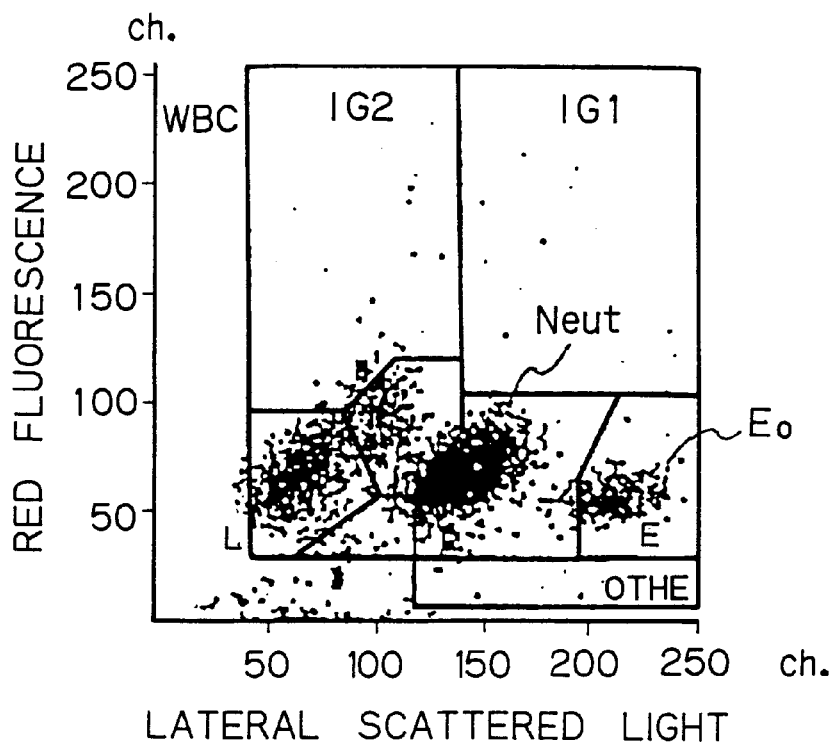
FIG. 22 is a lateral scattered light-fluorescence scattergram of a normal subject's blood sample measured using phthalic acid as an acid in Example 6.

FIG. 21 is a scattergram obtained using citric acid as the acid. FIG. 22 is a scattergram obtained using phthalic acid as the acid.

When phthalic acid (an organic acid having an aromatic ring in the molecular structure) was used as the acid, separation of neutrophils from eosinophils was improved compared with the use of citric acid.

According to the reagent for classification and counting of leukocytes of the present invention, a blood sample and a hemolytic agent are mixed, and mixed with the dye of the present invention to fluorescence stain nucleated cells in the blood sample. Then, at least one scattered light and at least one fluorescence are measured with a flow cytometer. Simply by so doing, abnormal cells such as immature leukocytes and abnormal leukocytes can be classified and counted easily and highly accurately, and at the same time, classification and counting of normal leukocytes as well as the counting of leukocytes can be performed.

What is claimed is:

1. A reagent for classification and counting of leukocytes, said reagent containing at least one dye which has the following structural formula

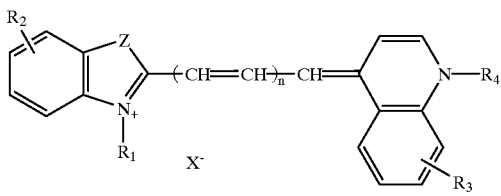

where $R_1$ is a hydrogen atom or an alkyl group, $R_2$ and $R_3$ each represent a hydrogen atom, a lower alkyl group or a lower alkoxy group, $R_4$ represents a hydrogen atom, an acyl group or an alkyl group, at least one of $R_1$ and R4 is an alkyl group having 8 to 18 carbon atoms, Z represents a sulfur atom, an oxygen atom, or a carbon atom having a lower alkyl group, n denotes 0, 1 or 2, and X represents an anion, and specifically binds to RNA to increase in fluorescence intensity.

2. A method for classification and counting 2 of leukocytes, comprising the steps of:

1) mixing a blood sample with a hemolytic agent which lyses erythrocytes in the blood sample to such a degree as not to impede measurement, thereby bringing normal or abnormal blood cells to a state suitable for staining;

2) mixing a sample prepared in the step 1) with a dye which has the following structural formula

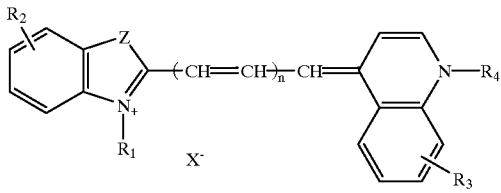

where $R_1$ is a hydrogen atom or an alkyl group, $R_2$ and $R_3$ each represent a hydrogen atom, a lower alkyl group or a lower alkoxy group, $R_4$ represents a hydrogen atom, an acyl group or an alkyl group, at least one of $R_1$ and $R_4$ is an alkyl group having 8 to 18 carbon atoms, Z represents a sulfur atom, an oxygen atom or a carbon atom having a lower alkyl group, n denotes 0, 1 or 2, and X represents an anion, and specifically binds to cellular RNA to increase in fluorescence intensity, thereby fluorescence-staining nucleated cells in the blood sample;

3) measuring an assay sample prepared in the step 2) with a flow cytometer to measure at least one scattered light and at least one fluorescence; and 4) classifying normal leukocytes into at least 5 populations, and counting them, by the use of differences in the intensities of the scattered light and the fluorescence measured in step 3).

3. The method for classification and counting of leukocytes as claimed in claim 2, wherein the hemolytic agent contains at least one nonionic surfactant and at least one cationic surfactant and has a pH of 4.5 to 11.0.

4. The method for classification and counting of leukocytes as claimed in claim 3, wherein the hemolytic agent further contains an organic acid having at least one aromatic ring or a salt thereof.

5. The method for classification and counting of leukocytes as claimed in claim 2, wherein the scattered light is at least one member selected from the group consisting of forward low-angle scattered light, forward high-angle scattered light, and lateral scattered light.

6. The method for classification and counting of leukocytes as claimed in claim 2, which can simultaneously perform the classification and counting of the abnormal blood cells.

7. The method for classification and counting of leukocytes as claimed in any one of claim 2 to 6, wherein the abnormal cells are cells with RNA content increased over the normal cells.

8. The method for classification and counting of leukocytes as claimed in claim 7, wherein the abnormal cells are one or more members selected from the group consisting of immature granulocytes, myeloblasts, erythroblasts and atypical lymphocytes.

9. A reagent kit for classification and counting of leukocytes, comprising:

1) a hemolytic agent which lyses erythrocytes in a blood sample to such a degree as not to impede measurement, thereby bringing normal or abnormal blood cells to a state suitable for staining; and 2) a staining solution containing at least one dye which has the following structural formula

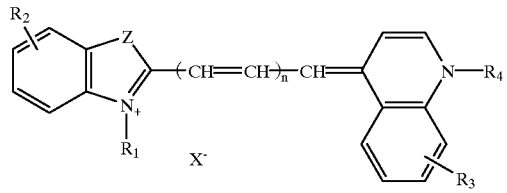

where $R_1$ is a hydrogen atom or an alkyl group, $R_2$ and $R_3$ each represent a hydrogen atom, a lower alkyl group or a lower alkoxy group, $R_4$ represents a hydrogen atom, an acyl group or an alkyl group, at least one of $R_1$ and $R_4$ is an alkyl group having 8 to 18 carbon atoms, Z represents a sulfur atom, an oxygen atom or a carbon atom having a lower alkyl group, n denotes 0, 1 or 2, and X represents an anion, and specifically binds to RNA to increase in fluorescence intensity.

* * * * *

UNITED STATES PATENT AND TRADEMARK OFFICE
CERTIFICATE OF CORRECTION

PATENT NO. : 6,004,816
DATED : December 21, 1999
INVENTOR(S) : Toshihiro Mitzukami It is certified that error appears in the above-identified patent and that said Letters Patent is hereby corrected as shown below:

Column 4,
Line 51, delete "In" and substitute -- in --;

Column 9,
Line 32, delete "(CDC$_{13}$)" and substitute -- (CDC$l_3$) --;
Line 35, delete "(cm$^{-6)}$:" and substitute -- (cm$^{-1}$) : --;
Line 61, delete "$^1$-NMR" and substitute -- $^1$H-NMR --;

Column 12,
Line 20, before the table insert -- A reagent of the following composition was prepared: --;

Column 13,
Line 20, after "counting" delete "2".

Signed and Sealed this

Twenty-first Day of May, 2002

Attest:

Attesting Officer

JAMES E. ROGAN
Director of the United States Patent and Trademark Office